(12) United States Patent
Van Saarloos et al.

(10) Patent No.: US 6,276,799 B1
(45) Date of Patent: Aug. 21, 2001

(54) STEREO OPTIC DISC ANALYZER

(75) Inventors: Paul Phillip Van Saarloos, Karrinyup; Robert Henry Eikelboom, Brookdale; Kanagasingam Yogesan, Nedlands, all of (AU)

(73) Assignee: The Lions Eye Institute of Western Australia Incorporated (DE)

( * ) Notice: Subject to any disclaimer, the term of this patent is extended or adjusted under 35 U.S.C. 154(b) by 0 days.

(21) Appl. No.: 09/548,132

(22) Filed: Apr. 12, 2000

Related U.S. Application Data

(63) Continuation of application No. PCT/AU98/00863, filed on Oct. 15, 1998.

(30) Foreign Application Priority Data

Oct. 15, 1997 (AU) .................................................. PO9819

(51) Int. Cl.⁷ ......................................................... A61B 3/14
(52) U.S. Cl. ............................................................. 351/206
(58) Field of Search ..................................... 351/205, 206, 351/211, 221; 600/407, 417, 440, 441, 443; 128/916; 345/30, 32, 419; 382/293, 294

(56) References Cited

U.S. PATENT DOCUMENTS 5,485,842 * 1/1996 Quistgaard ........................... 600/443
5,860,924 * 1/1999 Quistgaard ........................... 600/441

* cited by examiner

Primary Examiner—George Manuel
(74) Attorney, Agent, or Firm—Baker Botts LLP

(57) ABSTRACT

The present invention provides a system for creating and visualising three-dimensional images of an object, including imaging means for obtaining two images of the same object from different angles, digitizing means for digitizing the images, image processing means for color matching and registering the images, controller means for converting the two images into an interlaced image, display means for displaying the registered interlaced image, and visualizing means for visualizing the image in three dimensions. It also provides a method for creating and visualising three-dimensional images of an object including obtaining two images of the same object from different angles, digitizing the images, color matching and registering the images, converting the two images into an interlaced image, displaying the registered interlaced image for visualizing the image in three dimensions, measuring areas of interest, and calculating desired measurements of the object.

57 Claims, 3 Drawing Sheets

STEREO OPTIC DISC ANALYZER

This is a continuation of copending International application No. PCT/AU98/00863 filed Oct. 15, 1998.

The present invention relates to a computer imaging or vision technique for the creation and analysis of three dimensional images, of particular but not exclusive application in the creation and analysis of images of the retinal wall of the eye, and in other three dimensional medical and industrial imaging, including fields such as plastic surgery or aerial surveying and mapping. The invention also has application in the detection of anomalies of the ocular fundus, and in the early diagnosis, treatment and observation of diseases such as glaucoma and macular degeneration.

The ability to visualize objects in stereo, or in three dimensions, is a function of the position of the organs of sight, the eyes, and the manner in which the human brain processes visual information. The eyes are offset from one another, resulting in a slightly different view of an object being presented to each eye. The brain 'combines' the left and right perspectives, such that a single image, conveying information about depth, is perceived. Unlike the eye, conventional imaging methods, such as slide, film and video images, present only two dimensional images of an object.

The ocular fundus and optic disc possess, like most objects, a three dimensional structure. A better appreciation of fundus topography can, therefore, be gained from stereo photography and stereoscopic viewing. Stereo fundus photography can create three dimensional images of the optic nerve head. Using a fundus camera, the photographer produces two images of the ocular fundus, from the perspective of his or her left and right eye. The two images must then be aligned, and viewed with a stereo slide viewer, or a light table coupled with a pair of plus (+) lenses. Alternatively, the images may be projected through a polarised material onto a screen, with the stereo pair polarised at 90° to each other. The observer must view the images through polarising glasses with a polarising filter in front of each eye. These devices enable the left and right eye to "see" its corresponding image so that a stereo representation may be perceived (see Saine & Tyler (1997) for an overview of stereo imaging techniques).

Stereo examination of the ocular fundus provides useful information about the health of the eye, to guide diagnostic and treatment decisions. However, the clinician is most interested in observing the evolution of fundus topography over time. Comparing a patient's stereo fundus photographs at regular intervals may allow the clinician to review subtle changes in the architecture of the optic nerve head. However, these images, often taken at different times, by different people or in different lighting conditions, may possess variable characteristics, in terms of magnification, colour and the positioning of features in the image. These variations in image quality could be mistaken for changes in the topography of the optic nerve head.

Computer technology can overcome some of these problems through the use of image processing techniques. Colour matching techniques can eliminate colour and tonal differences between images of the same object taken on separate occasions, while image registration can minimise scale, translation and rotation variation. Regular computerized imaging of the ocular fundus is, therefore, a useful ophthalmic technique, enabling the clinician to make diagnostic decisions, track the course of a disease and to measure the effectiveness of treatment.

A number of digitized systems of image analysis have been developed to aid in the quantitative analysis of stereo images, such as that illustrated in U.S. Pat. No. 5,519,485. This patent describes a computerized, stereo image, measuring apparatus, suitable for topographical mapping and capable of displaying, and varying the magnification of, stereo images, and performing measurements relating to the three dimensional structure of the object being imaged. A control device or central processing unit controls the function of this system. Left and right images are introduced, from a scanner or the like, into two separate. optical disc drives. Images are displayed on a high resolution, stereo, display device comprising; a left and right monitor, a half mirror, a polarizing filter in front of each display unit and orthogonal polarized glasses worn by the observer. A feature extractor may be used to extract features from the image data through designated left and right measuring points.

U.S. Pat. No. 5,270,924 describes an ophthalmic image processing system that is able to recognize the difference between the left and right images of a stereo pair and to distinguish the top and bottom of the images, so that they may be stored without confusion. Another image processing system, the IMAGEnet, from Topcon Corporation, comprises a computerized image processing system for fluorescein angiography pictures, and fundus photography. This system may digitally enhance stereo images using sharpening and contrast stretching tools. Analysis functions, such as line area measurement, enable quantitative analysis of a number of separate images. However, this product has proven to be somewhat impractical in a clinical setting, as it requires long processing times and only registers images for translation differences in the X and Y directions.

Heidelberg Engineering have also developed a method of imaging the fundus of the eye, using software which captures images from a confocal scanning laser ophthalmoscope (cSLO). A cSLO image is constructed from a series of "slices" taken at varying levels of the fundus.

The slices are "stacked" together to form a single representation of fundus topography, with an accompanying sense of volume. To allow analysis of the same region of interest on respective slices, the operator defines this region with a contour line. This defined area then is stored and aligned on subsequent images. A topographical representation of the fundus is produced by determining height measurements at each location on the cSLO's multiple captured images. Estimates are then made of topographic variables, such as the mean height of the fundus contour, the optic cup volume and the volume of the optic nerve rim.

Quantitative analysis in the Heidelberg system is based on the intensity of the light reflected from the fundus. The area of highest reflectance is equivalent to the fundus contour, the edge surrounding the optic nerve head. At each level, or slice, the edge or fundus contour is determined, creating a topographic map of the fundus arnd enabling the calculation of the clinically important values outlined above. However, if a lesion or vessel in the slice is more reflective than the contour, the position of that lesion will be considered the position of fundus contour, a situation which may result in a misleading topographical picture.

Current computerised stereo imaging systems, such as those outlined above, may suffer from a number of practical disadvantages. Difficulties with image registration challenge the accuracy of analysis, while long processing times are a problem for clinical practice. Many of these systems produce only monochrome images which do not convey as much information as full colour images. In addition, none of the presently available systems provide a comparative measure for reviewing, in real time, three dimensional images in rapid sequence. There remains a need for an imaging system capable of producing full colour, registered, stereo images in real time. A novel, stereo imaging method and apparatus has therefore been developed, for constructing a three dimensional view of an object, and for performing quantitative analysis of the resultant stereo photographs. The present invention enables images of a three dimensional subject, such as the ocular fundus, to be viewed in stereo, and for serial comparison to take place between colour matched and registered images of the same object.

It is therefore an object of the present invention to provide an improved imaging system capable of producing a virtual, three dimensional representation of an object, that also enables an observer to compare representations of the object taken at different times.

It is a further object of the present invention to provide an improved stereo image processing system which has the ability to colour correct and automatically or semi-automatically register images in a stereo pair, or a set of stereo pairs, compensating for differences in size, rotation and translation between the stereo images.

According to the present invention there is provided a system for facilitating medical diagnosis by creating and visualising three dimensional images of the topography of an object, including:

imaging means for obtaining two images of the same object from different angles;

digitizing means for digitizing said images;

image processing means for colour matching and registering the images;

controller means for converting the two images into an interlaced image;

display means for displaying the registered interlaced image; and visualizing means for visualizing the image in three dimensions.

Preferably the system includes measuring means for measuring areas of interest in three dimensions, and calculating means for calculating desired measurements of the object.

Preferably, the display means and visualizing means are arranged for visualizing, in succession, said interlaced image and one or more corresponding images for said object obtained earlier, whereby to compare these images for determining changes in the topography of the object over time.

Preferably the system includes a stereo flicker chronoscope for effecting said visualizing of said interlaced image and said one or more corresponding images of said object obtained earlier.

Preferably the stereo flicker chronoscope is operable to serially display stereo pairs or sets of stereo pairs.

The stereo pairs or sets of stereo pairs may have been registered and/or colour corrected, by means of the image processing means.

The measuring means may be a three dimensional cursor.

Preferably the calculating means includes computer software.

Preferably the system includes result display means for displaying the results of the measurements.

Preferably the object is the ocular fundus of an eye and the result display means is a polar graph centred on the optic nerve head.

Preferably the imaging means is a stereo camera, a digital camera, a digital stereo camera, a video camera or a scanning laser ophthalmoscope operable to record two different views of the object to be imaged.

Preferably the digitizing means is a image scanner operable to digitize a slide film with high resolution, a digital camera, or any other apparatus operable to produce an image in, or convert an image into, a digital format.

Preferably the controller means is a computer or microprocessor.

Preferably the image processing means is software using the techniques of colour matching and image registration, and/or includes means for changing image magnification in three dimensions and real time.

Preferably the display means is a video display monitor or the like.

Preferably the visualizing means includes a pair of Liquid Crystal Display goggles.

The present invention also provides an apparatus for facilitating medical diagnosis by viewing three dimensional images of the topography of an object, including:

imaging means for obtaining first and second images of a stereo pair;

digitizing means for digitizing the two images;

image processing means for determining and correcting for colour, rotation, translation and scale differences between different images of the same object;

controller means for converting the images into a stereo interlaced image;

display means for displaying registered interlaced images; and visualizing means for visualizing the images in three dimensions.

Preferably the apparatus includes measuring means for measuring specific characteristics of the object, calculating means for calculating desired measurements of the object and result display-means for displaying the results of measurements.

Preferably, the display means and visualizing means are arranged for visualizing, in succession, said interlaced image and one or more corresponding images for said object obtained earlier, whereby to compare these images for determining changes in the topography of the object over time.

Preferably the apparatus includes a stereo flicker chronoscope for effecting said visualizing of said interlaced image and said one or more corresponding images of said object obtained earlier.

Preferably the stereo flicker chronoscope is operable to serially display stereo pairs or sets of stereo pairs.

Preferably the measuring means includes a three dimensional cursor.

Preferably the measuring means includes a circular or elliptical template that may be superimposed over each optic disc, and which may be used to measure one or more parameters including neuro-retinal rim width and optic disc cupping.

Preferably the calculating means includes computer software.

Preferably the first and second images are left and right images.

Preferably the display means is for displaying alternately an approximately equal number of one or more horizontal lines of the first image and of the second image.

Preferably the imaging means is a stereo camera, a digital camera, a digital stereo camera, a video camera, a scanning laser ophthalmoscope or any other suitable imaging means that is able to record two different views of the object to be imaged.

Preferably the digitizing means is an image scanner that is able to digitize a slide film with high resolution, a digital camera, or any apparatus capable of producing or converting image into a digital format.

Preferably the controller means is a computer or microprocessor.

Preferably the image processing means is custom software.

Preferably the image processing means uses colour matching and image registration methods for the correction of differences in colour, rotation, translation and scale, and/or includes means for changing image magnification in three dimensions and real time.

Preferably the methods includes a colour matching technique utilising a linear adjustment method to match the mean and standard deviation of each colour component, and an automatic or semi-automatic technique for rotation and translation effects.

Preferably the display means includes a video display monitor or the like.

Preferably the visualizing means includes a pair of Liquid Crystal Display goggles.

Preferably the goggles are Vrex wireless or 3D Max goggles, and more preferably the LCD goggles are electronically coupled to the display means.

Preferably the result display means includes a polar graph centred on the optic nerve head.

The present invention still further provides an apparatus for facilitating medical diagnosis by visualizing three dimensional, recreated views of the topography of an object, including:

- a stereo camera for obtaining first and second images of a stereo pair;
- digitizing means for digitizing the first and second images;
- image processing means for determining and correcting for colour, rotation, translation and scale differences between two different interlaced images of the same object;
- controller means for converting the images into an interlaced image, in which an approximately equal number of one or more horizontal lines of the first and then of the second image are displayed alternately;
- display means for displaying registered, interlaced images; and
- visualizing means for visualising the images in three dimensions.

Preferably the apparatus includes measuring means for measuring specific characteristics of the object, calculating means for calculating desired measurements of the object, and result display means for displaying the results of measurements.

Preferably, the display means and visualizing means are arranged for visualizing, in succession, said interlaced image and one or more corresponding images for said object obtained earlier, whereby to compare these images for determining changes in the topography of the object over time.

Preferably the apparatus includes a stereo flicker chronoscope for effecting said visualizing of said interlaced image and said one or more corresponding images of said object obtained earlier.

Preferably said object may be any object in which three dimensional topographic data is desirable.

Preferably said object includes human or animal tissue.

Preferably said object includes an animal or human body part.

Preferably said tissue or body part is the fundus of the eye, specifically the optic nerve head region, or other ocular features of interest.

According to the present invention there is also provided a method for facilitating medical diagnosis by creating and visualising three dimensional images of the topography of an object including:

- obtaining two images of the same object from different angles;
- digitizing said images;
- colour matching and registering the images;
- converting the two images into an interlaced image; and
- displaying the registered interlaced image for visualizing the image in three dimensions.

Preferably, the displaying step includes displaying, in succession for visualizing in three dimensions, said registered interlaced image and one or more corresponding images for said object obtained earlier, whereby to compare these images for determining changes in the topography of the object over time.

Preferably the method includes comparing stereo pairs or sets of stereo pairs, or colour correcting and/or registering and displaying sequentially or flickering two or more stereo pairs in 3D to highlight change or differences in topography.

Preferably the method includes displaying the results of the measurements.

Preferably said digitizing is performed in high resolution.

In order that the invention be more fully understood, some preferred embodiments will be described, by way of example, with reference to the following drawings in which.

Figure 1:
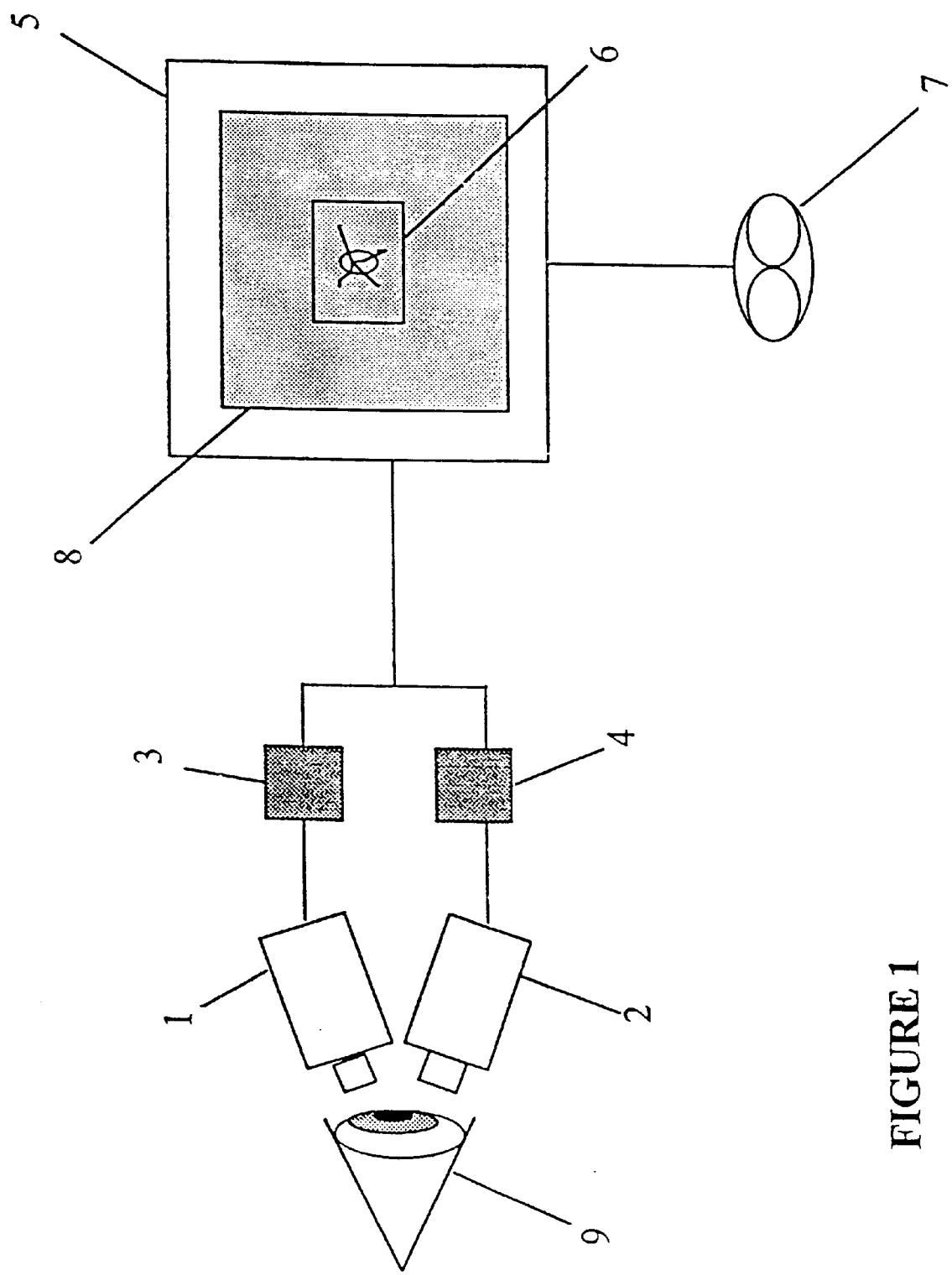
FIG. 1 is a diagrammatic plan view of a system according to the present invention.

Referring to FIG. 1, the first arrangement of an apparatus of the present invention includes a Nidek simultaneous stereo camera 1 and 2, for recording two different images 3 and 4, of the ocular fundus of patient's eye 9, taken from left and right viewing positions. Alternatively, the images may be captured on film and developed on photographic paper or slides, which may then be digitised for the controller means (see below) via a scanner, such as a Polaroid Sprintscan or the like.

Figure 2:
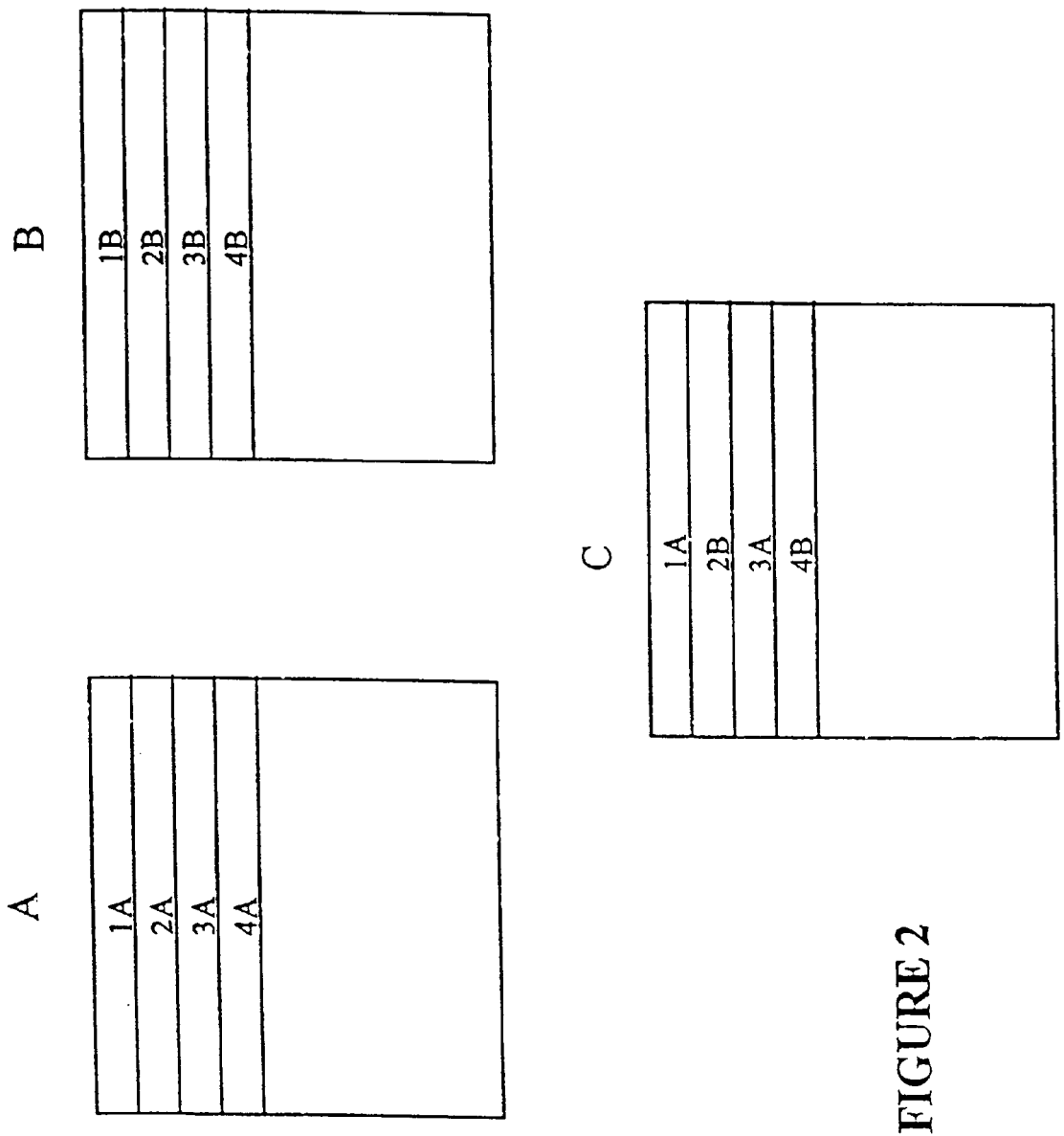
FIG. 2 is an explanatory diagram illustrating the process of producing an interlaced image.

An image file of digitized images 3 and 4 is generated and stored in the memory of a controller means in the form of an IBM compatible personal computer 5, although any appropriate computing system may be substituted. This image file is accessed via custom software. The left and right stereo images are converted by the software into a single interlaced image 6, in which every second line is captured from both images. Referring to FIG. 2, image A and image B are combined to form a single image C (corresponding to image 6 in FIG. 1) containing stereoscopic information. A horizontal line of pixels from image A is displayed as the first line of the interlaced image C, and a horizontal line from image B is displayed as the next line. Either image A or image B may be the left or right image. The process of capturing alternate lines of pixels from the two images continues until the completion of an interlaced image C. This image C, therefore, contains every second line of the right stereo image and every second line of the left image.

Liquid Crystal Display goggles 7 are then used to visualize the interlaced image 6 in stereo, on a display unit in the form of a computer monitor 8 or similar video display screen. The LCD glasses 7 may be electronically coupled to the display unit, such as with those made by 3 DMax, or they may be a wireless version, such as Vrex wireless LCD glasses. The monitor 8 must be in interlaced mode, so that firstly, the odd numbered horizontal lines are written on the display monitor, and then the even numbered horizontal lines. When the odd numbered lines are displayed, one of the two screens of the LCD goggles is darkened, while the other remains clear. The observer views the image with the eye under the clear screen and sees the information from the odd numbered lines (image A). After all of the odd numbered lines have been written, the LCD shutter alternates the darkened and clear vision windows and the even numbered lines are written (image B). This process takes approximately fifty milliseconds, which is imperceptible to the human eye. The interlaced image C can then be visualised as a "virtual" stereo image and the topography of the optic nerve head can be perceived in three dimensions. An alternative embodiment would involve a number of three dimensional glasses being connected, or used, in parallel with the video display monitor, so that several people could simultaneously view the interlaced image.

Figure 3:
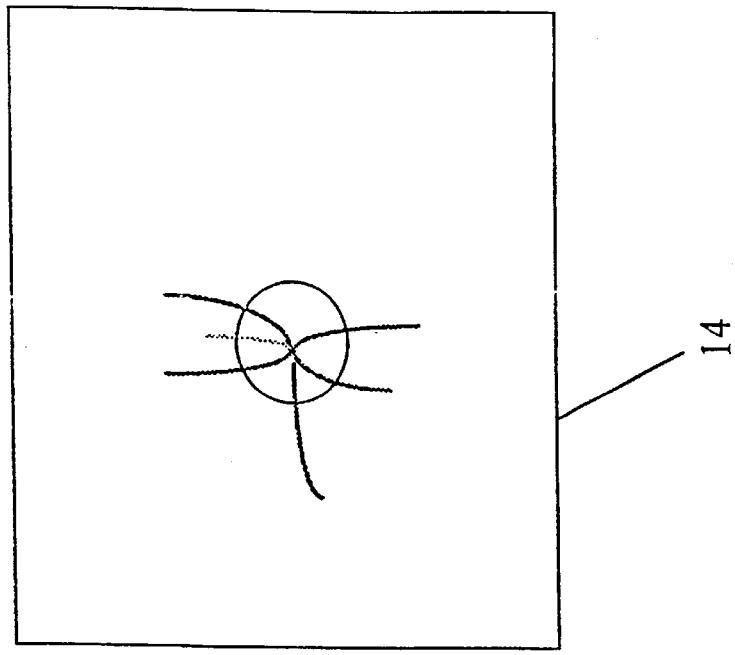
FIG. 3 is an illustration of a novel colour matching process according to a preferred embodiment of the present invention.
Figure 3:
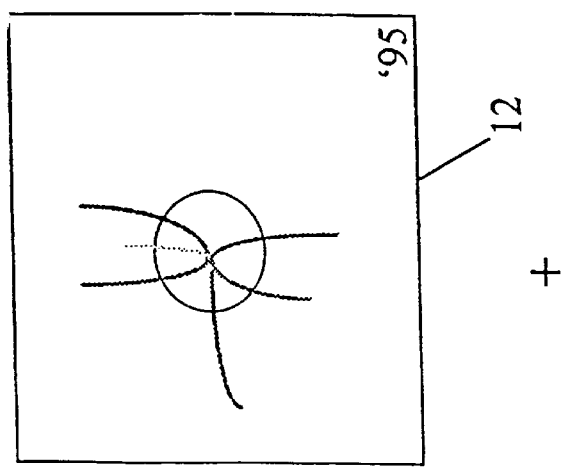
Figure 3:
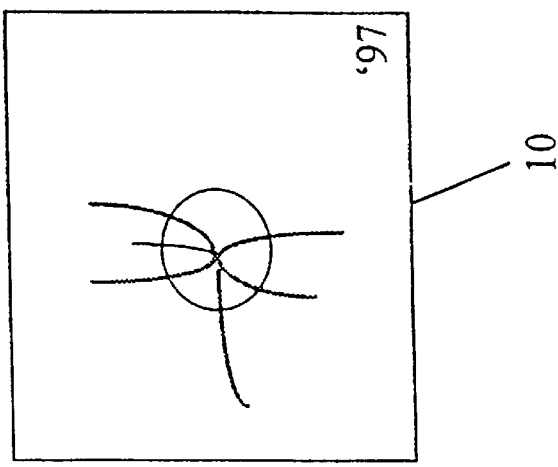

A novel image processing technique is incorporated into the custom software of PC 5 to compensate for differences in colour matching, scale, translation and rotation between stereo image pairs, or sets of stereo image pairs. FIG. 3 illustrates the technique through which colour matching is carried out. Linear adjustment is used to accommodate for differences in grey scale (colour) from one image of the same object to another. Linear adjustment of the input image 10, into the output image 14, occurs pixel by pixel, by calculation of the means and standard deviations from the reference image 12. For a grey scale image, this will simply adjust the mean and standard deviation of the input image to the mean and standard deviation of the reference image. For colour images, however, linear colour correction will be applied separately on each colour component of red, green and blue. The mean and standard deviation of each colour component of the input image will be appropriately matched to the reference image.

Image registration is also applied to compensate for translation, scale and rotation differences between stereo pairs or sets of stereo pairs. This may be completed via an automatic or a semi-automatic registration procedure.

Two different techniques may be used to align sequential input and reference images. The first method provides automated and precise image registration based on a normalized grey scale correlation. In this method, feature matching is obtained in both the input and reference images, whereby the same feature in both images is identified. A unique template is automatically selected from the input image and a similar template is identified, if it exists, from the reference or target image. The reference image is then registered according to the differences in the centre coordinates of the templates. To reduce the search time, the search area on the target image may be limited to double the size of the template surrounding the centre of the template. The normalized grey scale correlation function reaches a maximum value of 1 when the input and reference image match exactly, or 0 when there is no correlation. By moving the template over the reference image, the correlation function is computed at each position. The position where the largest correlation value is obtained is considered the best match.

A second technique uses a semi-automatic method to register the stereo pairs. An even number of points from the input image and the approximately corresponding points from the reference image are chosen. The best possible match for the points chosen on the reference image is found. The search area is limited to the area surrounding the points selected on the reference image. This may increase the speed as well as the accuracy of the correlation computation. The differences in the x and y directions for each point (input and reference points) are computed and the average of the differences in the x and y direction obtained. This will correct for any translation differences.

By connecting two points and calculating the angles with respect to a horizontal axis in the input and the reference image, the difference in the angle can also be obtained. The average angle difference for all the pairs of points will give an estimation for the overall rotation of the reference image. This technique is faster than the automatic method, but the fully automatic method may provide more accurate alignment.

The apparatus of the present invention can also supply means to view, in real time, registered, stereo images of the same fundus in rapid sequence (stereo flicker chronoscopy). This technique allows comparison of two or three dimensional fundus images from the same patient, taken on different occasions. For example, a stereo pair photographed in 1995 may be registered with a stereo image taken in 1997. As the display jumps from one image to the other, subtle changes in the structure of the optic disc can be easily perceived. Flickering between a number of registered images may help the clinician visualize any changes in fundus topography over time.

A three dimensional mouse pointer can also be used to manually measure structures of the optic nerve head or other areas of interest. The three dimensional mouse pointer is an indicator which can not only be moved back and forth across the image plane on the monitor, but also perpendicular to that plane. Using a keyboard or other controls (not shown in FIG. 1), the perceived depth of the pointer can be changed. This 3D mouse is valuable for measurements to be made or the precise location of objects or structures to be determined. It allows the cursor to be placed, in the eyes of the viewer, on the surface of the optic nerve or another three dimensional structure.

Measuring means, in the form of a circular or elliptic template, can then be displayed and positioned over the optic disc by the operator, to aid in obtaining measurements around the optic nerve head. Clinically important values regarding the extent of optic disc cupping and the width of the neuro-retinal rim can then be calculated. Differences in nerve-head rim measurements, between two chronologically separate images of the same fundus, can then be plotted in a polar fashion around the disc, with positive changes advancing beyond the edge of the disc and negative changes plotted towards the centre of the disc. A very good representation is thus displayed, allowing the operator to determine at a glance the size and position of any rim width changes. A quantitative measure of the change in optic nerve head rim measurements over time is therefore provided.

Thus, the present invention provides a novel system in which three dimensional images of an object may be constructed and analysed. Comparison between images taken at different times and at different orientations is possible using the present invention.

The advantages of the various embodiments of the apparatus and method of the present invention are thus that:

- stereo images can be seen on a screen, rather the clinician having to bend over a light box;
- a series of stereo images can be flickered ("stereo flicker chronoscopy"), which is not possible using only the slides, and without using a mechanical system such as a Deltascope;
- the edges of the optic disc, the start of optic disc cupping and the start of the floor of the optic cup can be seen much easier than from monoscopic images;

the high resolution allows precise location of the edges of the neuro-retinal rim;

colour adjustment and correction minimize errors due to change in colour of photographs attributable to the photographic process, pupil dilation, and lens changes;

the flicker system (chronoscopy) and the measurements system (chronometry) work together;

registered and colour adjusted images are stored, and so do not have to be done over and over again; and a number of people can observe the stereo image on the computer screen simultaneously.

Modification within the spirit and scope of the invention may therefore be readily effected by a person skilled in the art. Other alternative embodiments would involve the use of one or two video cameras or a scanning laser ophthalmoscope to directly capture the image in a digital format. Any other single or stereo camera or imaging device that is capable of creating an image of the optic nerve head from two viewing positions, simultaneously or sequentially, may also be utilised. Thus, it is to be understood that this invention is not limited to the particular embodiments described by way of example herein above.

What is claimed is:

1. A system for facilitating medical diagnosis by creating and visualizing three dimensional images of the topography of an object, including:

optical imaging means for optically obtaining two images of the same object from different angles;

digitizing means for digitizing said images;

image processing means for color matching and registering the images;

controller means for converting the two images into an interlaced image;

display means for displaying the registered interlaced image; and visualizing means for visualizing the image in three dimensions.

2. A system as claimed in claim 1, including measuring means for measuring areas of interest in three dimensions, and calculating means for calculating desired measurements of the object.

3. A system as claimed in claim 1, wherein said display means and visualizing means are arranged for visualizing, in succession, said interlaced image and at least one corresponding image for said object obtained earlier, whereby to compare these images for determining changes in the topography of the object over time.

4. A system as claimed in claim 3, including a stereo flicker chronoscope for effecting said visualizing of said interlaced image and said at least one corresponding image of said object obtained earlier.

5. A system as claimed in claim 4, wherein said stereo flicker chronoscope is operable to serially display stereo pairs.

6. A system as claimed in claim 2, wherein said measuring means is a three dimensional cursor.

7. A system as claimed in claim 2, wherein said calculating means includes computer software.

8. A system as claimed in claim 2, including result display means for displaying the results of the measurements.

9. A system as claimed in claim 8, wherein said object is the ocular fundus of an eye and said result display means is a polar graph centered on the optic nerve head.

10. A system as claimed in claim 1, wherein said imaging means is selected from the group consisting of a stereo camera, digital camera, a digital stereo camera, a video camera and a scanning laser ophthalmoscope operable to record two different views of the object to be imaged.

11. A system as claimed in claim 1, wherein said digitizing means is selected from the group consisting of an image scanner operable to digitize a slide film with high resolution, a digital camera, and any other apparatus operable to produce an image in, or convert an image into, a digital format.

12. A system as claimed in claim 1, wherein said controller means is a computer.

13. A system as claimed in claim 1, wherein said image processing means is software using the techniques of color matching and image registration, and includes means for changing image magnification in three dimensions and real time.

14. A system as claimed in claim 1, wherein said display means is a video display monitor.

15. A system as claimed in claim 1, wherein said object includes animal tissue.

16. A system as claimed in claim 1, wherein said object is an animal body part.

17. A system as claimed in claim 1, wherein said object is an ocular feature such as the fundus of an eye or the optic nerve head region.

18. A system as claimed in claim 1, wherein said visualizing means includes a pair of Liquid Crystal Display gogles.

19. An apparatus for facilitating medical diagnosis by viewing three dimensional images of the topography of an object, including:

imaging means for obtaining first and second images of a stereo pair;

digitizing means for digitizing the two images;

image processing means for determining and correcting for color, rotation, translation and scale differences between different images of the same object;

controller means for converting the images into a stereo interlaced image;

display means for displaying registered interlaced images; and visualizing means for visualizing the images in three dimensions.

20. An apparatus as claimed in claim 19, including measuring means for measuring specific characteristics of the object, calculating means for calculating desired measurements of the object and result display means for displaying the results of measurements.

21. An apparatus as claimed in claim 20, wherein said measuring means includes a three dimensional cursor.

22. An apparatus as claimed in claim 20, wherein said object is the ocular fundus of an eye and said measuring means includes a circular or elliptical template that may be superimposed over each optic disc, and which may be used to measure neuro-retinal rim width and optic disc cupping.

23. An apparatus as claimed in claim 20, wherein said calculating means includes computer software.

24. An apparatus as claimed in claim 20, wherein the result display means includes a polar graph centered on the optic nerve head.

25. An apparatus as claimed in claim 19, wherein said display means and visualizing means are arranged for visualizing, in succession, said interlaced image and one or more corresponding images for said object obtained earlier, whereby to compare these images for determining changes in the topography of the object over time.

26. An apparatus as claimed in claim 25, including a stereo flicker chronoscope for effecting said visualizing of said interlaced image and said one or more corresponding images of said object obtained earlier.

27. An apparatus as claimed in claim 25, wherein said stereo flicker chronoscope is operable to serially display stereo pairs or sets of stereo pairs.

28. An apparatus as claimed in claim 19, wherein said first and second images are left and right images.

29. An apparatus as claimed in claim 19, wherein the display means is for displaying alternately an approximately equal number of at least one horizontal line of the first image and of the second image.

30. An apparatus as claimed in claim 19, wherein said imaging means is selected from the group consisting of a stereo camera, a digital camera, a digital stereo camera, a video camera, a scanning laser ophthalmoscope and suitable imaging means capable of recording two different views of the object to be imaged.

31. An apparatus as claimed in claim 19, wherein said digitizing means is selected from the group comprising an image scanner for digitizing a slide film with high resolution, a digital camera, and an apparatus capable of converting an image into a digital format.

32. An apparatus as claimed in claim 19, wherein said controller means is a computer.

33. An apparatus as claimed in claim 19, wherein said image processing means is custom software.

34. An apparatus as claimed in claim 19, wherein said image processing means uses color matching and image registration methods for the correction of differences in color, rotation, translation and scale, and includes means for changing image magnification in three dimensions and real time.

35. An apparatus as claimed in claim 19, wherein said display means includes a video display monitor.

36. An apparatus as claimed in claim 34, wherein said image processing means further provide a color matching technique utilizing a linear adjustment method to match the mean and standard deviation of each color component, and an automatic or semi-automatic technique for rotation and translation effects.

37. An apparatus as claimed in claim 19, wherein said visualizing means includes a pair of Liquid Crystal Display goggles.

38. An apparatus as claimed in claim 37, wherein said goggles are Vrex wireless of 3-D Max goggles.

39. An apparatus as claimed in claim 37, wherein said LCD goggles are electronically coupled to the display means.

40. An apparatus as claimed in claim 19, wherein said object includes animal tissue.

41. An apparatus as claimed in claim 19, wherein said object is an animal body part.

42. An apparatus as claimed in claim 19, wherein said object is an ocular feature such as the fundus of an eye or the optic nerve head region.

43. An apparatus for facilitating medical diagnosis by visualizing three dimensional, recreated views of the topography of an object, including:
a stereo camera for obtaining first and second images of a stereo pair;
digitizing means for digitizing the first and second images;
image processing means for determining and correcting for color, rotation, translation and scale differences between two different interlaced images of the same object;
controller means for converting the images into an interlaces image, in which an approximately equal number of at least one horizontal line of the first and then of the second image are displayed alternately;
display means for displaying registered, interlaced images; and
visualizing means for visualizing the images in three dimensions.

44. An apparatus as claimed in claim 43, including measuring means for measuring specific characteristics of the object, calculating means for calculating desired measurements of the object, and result display means for displaying the results of measurements.

45. An apparatus as claimed in claim 43, wherein said display means and visualizing means are arranged for visualizing, in succession, said interlaced image and at least one corresponding image for said object obtained earlier, whereby to compare these images for determining changes in the topography of the object over time.

46. An apparatus as claimed in claim 45, including a stereo flicker chronoscope for effecting said visualizing of said interlaced image and said at least one corresponding image of said object obtained earlier.

47. An apparatus as claimed in claim 43, wherein said first and second images are left and right images.

48. An apparatus as claimed in claim 43, wherein said object is an object in which three dimensional topographic data is desirable.

49. A method for facilitating medical diagnosis by creating and visualizing three dimensional images of the topography of an object, including:
obtaining two images of the same object from different angles;
digitizing said images;
color matching and registering the images;
converting the two images into an interlaced image; and
displaying the registered interlaced image for visualizing the image in three dimensions.

50. A method as claimed in claim 49, including comparing stereo pairs.

51. A method as claimed in claim 49, including the steps of highlighting differences in topography selected from the group comprising color correcting, registering and displaying sequentially, and flickering at least two stereo pairs in 3D.

52. A method as claimed in of claim 49, wherein said digitizing is performed in high resolution.

53. A method according to claim 49, further including measuring areas of interest in said registered interlaced image, and calculating desired measurements of the object.

54. A method as claimed in claim 53, including displaying the results of said measurements.

55. A method as claimed in claim 49, wherein said displaying step includes displaying, in succession for visualizing in three dimensions, said registered interlaced image and at least one corresponding image for said object obtained earlier, whereby to compare these images for determining changes in the topography of the object over time.

56. A method as claimed in claim 49, wherein said object includes animal tissue.

57. A method as claimed in claim 49, wherein said object is an ocular feature such as the fundus of an eye or the optic nerve head region.

* * * * *

UNITED STATES PATENT AND TRADEMARK OFFICE
CERTIFICATE OF CORRECTION

PATENT NO. : 6,276,799 B1
DATED : August 21, 2001
INVENTOR(S) : Van Saarloos et al.

It is certified that error appears in the above-identified patent and that said Letters Patent is hereby corrected as shown below:

Column 1,
Line 50, "lighting" should read -- lighting --

Column 2,
Line 10, "comprising;" should read -- comprising: --
Line 51, "arnd" should read -- and --

Column 3,
Line 60, "centred" should read -- centered --

Column 4,
Line 31, "display-means" should read -- display means --

Column 5,
Line 23, "centred" should read -- centered --

Column 6,
Line 67, "3 DMax" should read -- 3DMax --

Column 9,
Lines 25 and 58, "three dimensional" should read -- three-dimensional --

Column 10,
Line 27, "gogles." should read -- goggles. --
Lines 29 and 51, "three dimensional" should read -- three-dimensional --
Line 36, "¶translation" should read -- translation -- (append to previous line)

Column 11,
Line 45, "of" should read -- or --
Line 57, "three dimensional" should read -- three-dimensional --; and "recreated" should read -- re-created --

UNITED STATES PATENT AND TRADEMARK OFFICE
CERTIFICATE OF CORRECTION

PATENT NO. : 6,276,799 B1
DATED : August 21, 2001
INVENTOR(S) : Van Saarloos et al.

It is certified that error appears in the above-identified patent and that said Letters Patent is hereby corrected as shown below:

Column 12,
Line 2, "laces" should read -- laced --
Lines 27 and 30, "three dimensional" should read -- three-dimensional --
Line 47, "of" should be deleted Signed and Sealed this Third Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,276,799 B1
DATED : August 21, 2001
INVENTOR(S) : Paul Phillip Van Saarloos et al.

It is certified that error appears in the above-identified patent and that said Letters Patent is hereby corrected as shown below:

<u>Title page,</u>
Item [73], Assignee, "(DE)" should read -- (AU) --

Signed and Sealed this

Twelfth Day of August, 2003

JAMES E. ROGAN
*Director of the United States Patent and Trademark Office*